US011717666B2

(12) United States Patent
Desombre et al.

(10) Patent No.: US 11,717,666 B2
(45) Date of Patent: Aug. 8, 2023

(54) CONNECTOR DEVICE FOR GASTRIC CALIBRATION HOSES, AS WELL AS MEDICAL SYSTEM COMPRISING A CONNECTOR DEVICE FOR GASTRIC CALIBRATION HOSES AND A GASTRIC CALIBRATION HOSE

(71) Applicant: Q Medical International AG, Stein am Rhein (CH)

(72) Inventors: Rainer Desombre, Meerbusch (DE); Eugenius Eisenzimmer, Kaiserslautern (DE)

(73) Assignee: Q MEDICAL INTERNATIONAL AG, Stein am Rhein (CH)

( * ) Notice: Subject to any disclaimer, the term of this patent is extended or adjusted under 35 U.S.C. 154(b) by 135 days.

(21) Appl. No.: 16/152,746

(22) Filed: Oct. 5, 2018

(65) Prior Publication Data

US 2019/0105483 A1 Apr. 11, 2019

(30) Foreign Application Priority Data

Oct. 6, 2017 (EP) .................................... 17195241

(51) Int. Cl.
*A61M 39/10* (2006.01)
*A61F 5/00* (2006.01)
*A61M 39/08* (2006.01)

(52) U.S. Cl.
CPC ............ *A61M 39/10* (2013.01); *A61F 5/0089* (2013.01); *A61M 39/08* (2013.01); *A61M 2039/1027* (2013.01); *A61M 2039/1083* (2013.01)

(58) Field of Classification Search
CPC ........ A61M 25/0147; A61M 2025/015; A61M 39/08; A61M 39/10; A61M 39/12;
(Continued)

(56) References Cited

U.S. PATENT DOCUMENTS 2,498,692 A * 2/1950 Marshall ............. A61J 15/0003
604/95.04
3,780,740 A * 12/1973 Rhea .................... A61J 15/0026
604/270
(Continued)

FOREIGN PATENT DOCUMENTS

CN 201120030 Y 9/2008
CN 204260838 U 4/2015
(Continued)

OTHER PUBLICATIONS

European Search Report dated Apr. 9, 2018 of corresponding application No. EP17195241.9; 7 pgs.
(Continued)

*Primary Examiner* — Kami A Bosworth
(74) *Attorney, Agent, or Firm* — Maier & Maier, PLLC

(57) ABSTRACT

A connector device for gastric calibration hoses, including a first end and a second end opposite the first end. A first connector is disposed at the first end and a second connector is disposed at the second end. The first and the second connector are connected with each other via a fluid channel. The first connector includes a first tapering cavity sized and shaped to receive and couple with a gastric calibration hose. The second connector includes a second tapering cavity and a tapering recess annularly surrounding the second tapering cavity. The second tapering cavity and the tapering recess are sized and shaped to alternatively couple with different medical devices by receiving therein tubular structures of the different medical devices.

16 Claims, 6 Drawing Sheets

(58) Field of Classification Search
CPC ...... A61M 2039/082; A61M 2039/085; A61M 2039/1027; A61M 2039/1077; A61M 2039/1083; A61M 2039/1088; A61M 2039/1094; A61M 2210/1053; A61M 2039/0009; A61M 2210/1057; A61M 2210/106; A61M 2210/1064; A61F 5/0003; A61F 5/0013; A61F 5/0036–0046; A61F 5/0089; A61F 2005/0016–23; A61J 15/00; A61J 15/0003; A61J 15/0015–0023; A61J 15/0026; A61J 15/0069; A61J 15/0073; A61J 15/0092
See application file for complete search history.

(56) References Cited

U.S. PATENT DOCUMENTS

| | | | |
|---|---|---|---|
| 4,163,722 A * | 8/1979 | Cosentino | A61M 39/10 |
| | | | 210/236 |
| 4,511,163 A | 4/1985 | Harris et al. | |
| 4,525,156 A * | 6/1985 | Benusa | A61M 1/0058 |
| | | | 604/28 |
| 5,776,117 A | 7/1998 | Haselhorst et al. | |
| 5,947,120 A * | 9/1999 | Bailey | A61M 16/0463 |
| | | | 128/207.14 |
| 6,808,521 B1 * | 10/2004 | McMichael | A61J 15/0026 |
| | | | 285/148.23 |
| 2006/0111612 A1 * | 5/2006 | Matsumoto | A61B 1/00101 |
| | | | 600/129 |
| 2009/0326481 A1 * | 12/2009 | Swisher | A61J 15/0026 |
| | | | 604/246 |
| 2010/0022951 A1 * | 1/2010 | Ferrera | A61M 39/0613 |
| | | | 604/103 |
| 2012/0029465 A1 * | 2/2012 | Wu | A61M 5/165 |
| | | | 604/500 |
| 2015/0032089 A1 * | 1/2015 | Way | A61M 39/1011 |
| | | | 604/535 |
| 2017/0014616 A1 * | 1/2017 | Davis | A61M 31/00 |

FOREIGN PATENT DOCUMENTS

| | | |
|---|---|---|
| EP | 1629764 A1 | 3/2006 |
| WO | 2002/18005 A1 | 3/2002 |
| WO | 2009/021030 A1 | 2/2009 |
| WO | 2011/066586 A1 | 6/2011 |
| WO | 2011066586 A1 | 6/2011 |
| WO | 2016/158937 A1 | 10/2016 |
| WO | 2016158937 A1 | 10/2016 |

OTHER PUBLICATIONS

Chinese Office Action dated Nov. 3, 2020, in connection with corresponding CN Application No. 201811167527.8 (8 pp., including machine-generated English translation).

Office Action dated Mar. 2, 2022 in Chinese Patent Application No. 2018111675278 (with English translation); 11 pgs.

Office Action dated Jul. 12, 2022 in corresponding Mexican Patent Application No. MX/a/2018/012080 (with English translation); 7 pgs.

Office Action dated Oct. 20, 2022, in corresponding Mexican Application No. MX/a/2018/012080, 16 pages.

* cited by examiner

CONNECTOR DEVICE FOR GASTRIC CALIBRATION HOSES, AS WELL AS MEDICAL SYSTEM COMPRISING A CONNECTOR DEVICE FOR GASTRIC CALIBRATION HOSES AND A GASTRIC CALIBRATION HOSE

FIELD

The invention relates to a connector device for gastric calibration hoses, as well as medical system comprising a connector device for gastric calibration hoses and a gastric calibration hose.

BACKGROUND

From the field of medicine connector devices are generally known by which fluid connections can be made between different fluid-conveying medical devices (such as e.g. syringes, cannulas, catheters, three-way valves and other tubular structures).

Here, it is known that, at their opposite ends, the connector devices have a first and a second means, respectively, for coupling the different medical devices thereto. Upon coupling, a detachable fluid connection is made between the different devices. The sealing between the parts to be coupled is frequently secured by means of conical surfaces adapted to each other.

It is a drawback of the connector devices known from prior art that only a specific medical device can be coupled to the connector devices, respectively. As a consequence, connector devices have to be used that are respectively adapted to the dimensions of the medical devices used.

Further, gastric calibration hoses are known from prior art for use in performing medical laparoscopic surgical procedures, such as in particular in the context of surgical techniques like e.g. the biliopancreatic diversion with duodenal switch (LBPD-DS), the banded Roux-en-Y gastric bypass (LBRYGB), the banded sleeve gastrectomy (LBSG), the conventional sleeve gastrectomy (LCSG), the conventional Roux-en-Y gastric bypass (LCRYGB) and the banded gastric bypass.

At their first/proximal hose end directed to the attending physician, the above-mentioned gastric calibration hoses comprise a connector device for coupling medical devices to the gastric calibration hose. Via their first end, the connector devices are connected to the gastric calibration hose in the region of the first/proximal hose end. At their second end averted from the calibration hose, the connector devices connected to the gastric calibration hoses comprise a means for coupling medical devices. Here, the coupling means comprises a fixedly defined geometry such that only medical devices can be coupled thereto that have corresponding dimensions and/or connection geometries compatible with the coupling means.

It is a drawback of the above prior art that only those medical devices can be connected to the calibration hose which respectively have the correct, fixedly defined geometries.

However, in the context of the medical operations to be performed with the gastric calibration hose, it is necessary or desired to couple different medical devices thereto, such as e.g. different syringes, cannulas and/or suction hoses having different geometries.

In this regard it is a problem that the above-mentioned medical devices must all have the same dimensions in the region of the coupling means, which is possible only to a limited extend, e.g. with different cannulas or syringe sizes, such that further adapter elements are regularly required for coupling the above-mentioned medical devices.

SUMMARY

Therefore, it is an object of the invention to provide a connector device for gastric calibration hoses, as well as a medical system comprising a connector device for calibration hoses, as well as a gastric calibration hose, which does not have the above-mentioned drawbacks of the prior art, and to guarantee a simple and secure coupling of different medical devices having various connection geometries.

The object is achieved with the features of claim 1 and claim 9, respectively.

According to the invention a connector device for gastric calibration hoses has a first and an opposite second end, wherein a first connector means is formed at the first end and a second connector means is formed at the second end, wherein the first and the second connector means are connected with each other via a fluid channel, and wherein the first connector means comprises at least one first tapering cavity into which gastric calibration hoses may be plugged for coupling.

The connector device of the invention is characterized in that, for coupling different medical devices, the second connector means has at least one second tapering cavity and at least one, tapering recess annularly surrounding the second cavity, so that, for coupling, the different medical devices may selectively be plugged into the second tapering cavity or into the tapering recess.

The connector device may comprise a substantially cylindrical body having a body longitudinal axis, wherein the first and the second connector means may be arranged at opposite first and second ends of the cylinder. In a preferred embodiment, the body forming the connector device may be of a circular cylindrical design. Here, the connector device may in particular have a longitudinal axis and the fluid channel may substantially extend parallel to the longitudinal axis of the connector device.

The different medical devices may e.g. be syringes, cannulas, fingertips, as well as tubular structures such as e.g. suction hoses. In this regard it is decisive that the different medical devices each have a connector means formed thereto which, however, due to the different dimensions of the above-mentioned medical devices may also have clearly different dimensions and may, in addition, also have different geometrical designs.

A fingertip is a fluid channel with two opposite connector means, as well as a lateral opening at the fluid channel. When the fingertip is interposed between a vacuum source (suction pump) and a suction hose or calibration hose, the suction effect in the suction hose or the calibration hose can be regulated as desired via the lateral opening of the fingertip. By repeatedly clearing and blocking the lateral opening, e.g. by means of the tip of a finger, an intermittent suction process can be obtained.

The term coupling as used herein is to be understood as establishing a detachable fluid connection between the different medical devices to be coupled and the connector device.

The first and/or the second tapering cavity are each in fluid communication with the fluid channel at their end which is located in the connector device and thus is averted from the hose end. Thus, the first and/or the second tapering cavity may also be considered a part of the fluid channel. The first and/or the second tapering cavity may have substantially the same dimensions as the fluid channel at the transition to the fluid channel. In an alternative embodiment, however, it is also conceivable that a change in diameter is provided at the transition between the first and/or the second tapering recess and the fluid channel, such that a step is formed at the transition.

The design of the connector device according to the invention has the advantage that different medical devices with different connector systems and in particular also different connection geometries may be coupled in the region of the second connector means. In particular, this has the advantage that, while using a gastric calibration hose having a connector device of the present invention, a physician can use different medical devices with in particular different connection geometries without having to change the connector device coupled to the gastric calibration hose and without having to use adapters—

A plurality of different medical devices with different connection geometries and/or systems may be coupled via the second connector means, so that a use of additional adapter pieces can be avoided altogether. Further, it is now possible for an attending physician to use the respective required medical devices, such as e.g. syringes with different volumes, fingertips or suction hoses, while using the calibration hose, and the second connector means ensures that any of the above-mentioned medical devices can be coupled directly to the connector device. The design according to the invention thus opens up the possibility for hospital staff or an attending physician to flexibly choose among most different medical devices.

In a preferred embodiment the first cavity may taper from the first end towards the second end and/or the second cavity may taper from the second end towards the first end.

The tapered design of the first and/or the second cavity has the advantage that the medical devices to be coupled via the first and/or the second cavity can simply be introduced into the region of the first or second connector means. The tapered design of the cavity further has the advantage that, upon the introduction of the medical devices into the tapering cavity, the device to be coupled automatically centers and aligns itself in the cavity such that a canting of the medical device to be coupled is largely avoided. In this regard, it may be provided that the required sealing between the tapering cavity and the medical device to be coupled is ensured by the fact that the medical device to be coupled has an outer surface contour adapted to the contour of the tapering cavity.

The first tapering cavity and/or the second tapering cavity may form a part of the fluid channel.

According to another design it may be provided that the opposite first and second tapering cavities smoothly merge with each other at their end averted from the hose end, such that the proper fluid channel of the connector device is formed only by the opposite tapering cavities. Such a design has the advantage that the size and in particular the length of the connector device can be kept small. Thus, particularly compact embodiments of connector devices can be realized.

In a preferred embodiment a delimiting wall and an outer wall surrounding the recess may be formed between the second cavity and the recess, wherein the outer wall is designed to be set back towards the second end with respect to the delimiting wall, such that the delimiting wall forms the first end. The above embodiment has the advantage that the second connector means is provided with two different coupling means. The first coupling possibility is formed by the tapering cavity or the inner cone. A further coupling possibility, which is independent of the former one, is formed by the recess enclosed between the delimiting wall and the outer wall.

It may advantageously be provided that an outer diameter of the delimiting wall increases from the second end towards the first end. Due to the increasing outer diameter of the delimiting wall, the same may be used as a further possibility for coupling medical devices with an inner cone or recess. Further, due to the increasing outer diameter, devices to be coupled can be pushed onto the delimiting wall and be guided into the region of the recess more easily.

Further, it may be provided that the delimiting wall is chamfered in the region of the second end.

Here, the chamfer of the delimiting wall is such that the delimiting wall has an end face which is inclined with respect to the longitudinal axis of the connector device such that an angle other than 90° is included between the inclined plane of the end face and the body longitudinal axis of the connector device. The chamfer of the delimiting wall has the advantage that the opening formed at the end of the delimiting wall is delimited by an oval or elliptic transversal end wall surface. The transversal oval end wall surface facilitates the introduction of medical devices into the opening or into the recess surrounded by the delimiting wall.

It may further be provided that the annular recess continuously tapers from the second end towards the first end, wherein the dimensions of the recess are adapted to the average wall thickness of the medical devices to be coupled to the second connector means.

The above continuously tapering design of the annular recess has the advantage that medical devices with tubular structures without a particular connection system and with different wall thicknesses can be coupled directly to the connector device via the second connector means. Upon coupling, the hose wall is introduced into the recess until the wall is clamped between the delimiting wall and the outer wall; the clamping at the same time provides for sealing.

In a particularly preferred embodiment it may be provided that the dimension of the first cavity is adapted to an outer diameter of the gastric calibration hose to be coupled thereto.

It is preferred that the first cavity is designed for coupling gastric calibration hoses with an outer diameter in a range between ca. 30 to 45 Fr (French).

According to another preferred embodiment, the dimension of the first cavity is adapted for coupling a calibration hose with an outer diameter of 32, 34, 36, 38 or 40 Fr (French).

The term "French", abbreviated as "Fr", defines a measure for the outer diameter of tubular structures, such as e.g. cannulas or calibration hoses. Three French equal exactly one millimeter, or 1 Fr=⅓ mm. Thus, the Fr number is always three times the outer diameter in millimeters. In the French language area, the term "Charrière", abbreviated as "Ch", is used as a synonym of the term "French". In the US language area, the outer diameter of tubular structures the measuring unit "Gauge", abbreviated as "G" is used as well, which, however, does not correspond to the measures in Charrière or French.

The below inserted table shows the basic relation between the different measurement scales:

| French [ ] | Gauge [ ] | Outer diameter [mm] |
|---|---|---|
| 1 | 29 | 0.33 |
| 2 | 23 | 0.635 |
| 3 | 29 | 1.067 |
| 4 | 18 | 1.27 |
| 5 | 16 | 1.651 |
| 10 | 10 | 3.404 |

Given a circular cylindrical design of the connector device, the first cavity can be designed as an inner cone, wherein the inner cone has a maximum opening diameter in the region of the second end of the connector device and tapers along its extension towards the first end down to a second minimum diameter.

It may be provided that, from the first end towards the second end, the first cavity comprises at least two contiguous, respectively tapering steps for receiving gastric calibration hoses with different average diameters, wherein the steps have different initial and end diameters, and wherein the respective average diameter of the steps respectively decreases continuously from the first end towards the second end.

The step-shaped design of the first cavity with respectively different average diameters allows for the coupling of different gastric calibration hoses with different average outer diameters via the different steps of the first cavity.

In another preferred embodiment it may be provided that the first cavity comprises an inclined chamfer at the first end.

The chamfer has a surface extending from the second end towards the first end and being inclined inward from the outside. The chamfer has the advantage that the gastric calibration hoses to be coupled via the first cavity can be inserted more easily into the first cavity. Due to the chamfer, the calibration hose is centered as it is introduced into the first cavity, whereby a jamming or skewing of the calibration hose is avoided during insertion.

It may further be provided that chamfers are respectively arranged in the region of the opening diameters of the tapering steps of the first cavity.

According to the invention a medical system comprises a connector device for calibration hoses, as well as a gastric calibration hose, wherein the gastric calibration hose has at least a hose longitudinal axis, a first and an opposite second hose end and a hose wall that encloses a lumen, wherein an end element is arranged at the second end, delimiting the lumen, wherein the end element comprises at least one passage extending through the end element in a manner substantially parallel to the hose longitudinal axis, wherein the first hose end is coupled to the connector device via the first connector means.

According to the invention a gastric calibration hose may comprise at least a hose longitudinal axis, a first and an opposite second hose end, and a hose wall, hat encloses a lumen, wherein an end element is arranged at the second end, delimiting the lumen, wherein the end element comprises at least one passage and/or an opening extending through the end element in a manner substantially parallel to the hose longitudinal axis.

The first hose end may substantially be formed by a hose opening which itself is formed merely by the end of the hose wall, such that the lumen is formed at the first end.

The gastric calibration hose may preferably have a length in the range from ca. 1,000 mm to 1,300 mm.

In this regard, the above-mentioned medical system has the advantage that a plurality of different medical devices with different geometries can be coupled to the gastric calibration hose.

In an advantageous embodiment it may be provided that the hose wall has a plurality of openings in the region of the second hose end. The plurality of openings reduces or may even completely prevent the formation of an obstruction when a vacuum is generated in the lumen of the calibration hose. Due to the plurality of openings the prevailing vacuum is distributed to a plurality of openings such that the suction force acting on possibly drawn body tissue in the region of the openings, and thus the risk of injury, can be reduced significantly.

The hose wall of the gastric calibration hose may preferably have an outer diameter in the range from ca. 30 to 45 Fr (French).

According to another preferred embodiment the calibration hose has a hose wall with an outer diameter of 32, 34, 36, 38 or 40 Fr (French). The hose wall of the gastric calibration hose may be provided with a color stripe along the hose longitudinal axis, wherein the color of the stripe differs for different outer diameters. The color encoding has the advantage that confusion of sizes of the calibration hoses can be avoided.

The hose wall may be provided with length markers along the longitudinal axis. The length markers allow the attending physician or the anesthetist to determine what part of the hose length has already been introduced into the body of a patient to be treated.

It may be provided that the end element has a rounded and/or semi-spherically shaped surface at the end averted from the hose. The rounded and/or semi-spherically shaped surface has the advantage that upon insertion of the gastric calibration hose the same adapts more easily to the course of body openings and a buck-ling or "kinking", as it is referred to by those skilled in the art, is essentially pre-vented. In addition, the semi-spherically shaped surface can essentially avoid injuries to body tissue when the end element hits and/or bumps against a body wall.

The end element may be made of a material that has a lower rigidity than the hose wall of the gastric calibration hose. In particular, it may also be provided that the end element has a lower Shore hardness than the hose wall of the gastric calibration hose.

In this regard fabricating the end element from a flexible plastic material has the advantage that when advancing the gastric calibration hose, and thus during a forward movement of the end element, in the body cavities injuries to a body wall are essentially avoided when the end element hits and/or bumps against a body wall. Making the end element from a flexible plastic material further has the advantage that the end element acts as a kind of buffer for the gastric calibration hose. In the event of the end element hitting against a body tissue, the end element absorbs the kinetic energy of the gastric calibration hose by a deformation of the flexible end element.

In another preferred embodiment it may be provided that the end element at least partly comprises a radiopaque material. Forming the end element with a radiopaque material has the advantage that the position of the gastric calibration hose can be identified clearly within the body using imaging X-ray methods. The attending physician can thus clearly determine, whether the gastric calibration hose has been introduced to the desired position in the body. The end element may include barium sulfate, for example.

It may further be provided that the end element is colored blue at least in part.

Using minimally invasive imaging methods, e.g. video endoscopy, the end element colored in blue can be identified clearly in the body of a patient to be treated, since no blue-colored objects exist in the human body.

In a particularly preferred embodiment it may be provided that the gastric calibration hose comprises at least one auxiliary channel, wherein the at least one auxiliary channel encloses a volume and extends substantially parallel to the hose longitudinal axis, wherein a first end of the at least one auxiliary channel ends at the outer hose wall in the region of the first hose end, and wherein a second end of the at least one auxiliary channel opens into the end element.

The volume enclosed by the at least one auxiliary channel is completely sealed from the lumen of the gastric calibration hose, such that no fluid connection exists between the volume of the auxiliary channel and the lumen of the gastric calibration hose.

In this regard it may be provided that the at least one auxiliary channel is arranged inside and/or outside the calibration hose as an auxiliary hose. In particular, it may be provided that the auxiliary channel is arranged in the region of the inner wall of the calibration hose. In a particularly preferred embodiment it may be provided that the at least one auxiliary channel is formed integrally with the hose wall of the calibration hose, such that the lumen of the calibration hose is divided into a plurality of lumens by forming a plurality of partition walls in the calibration hose.

It may be provided that a light conductor means is provided in at least one auxiliary channel, wherein a light entry surface is formed at the light conductor device in the region of the first hose end, and wherein, in the second hose end, the light conductor device extends through the end element to the end averted from the hose, where a light emission means is arranged.

Providing the light conductor means has the advantage that light waves can be conducted into the region of the end element via the conductor means, such that the region in front of the end element of the gastric calibration hose can be illuminated, wherein the light beams are emitted from the light emission means in the region of the end element.

BRIEF DESCRIPTION OF THE DRAWINGS

The following is a detailed explanation of different embodiments of the invention with reference to the drawings.

The Figures show.

DETAILED DESCRIPTION

Figure 1:
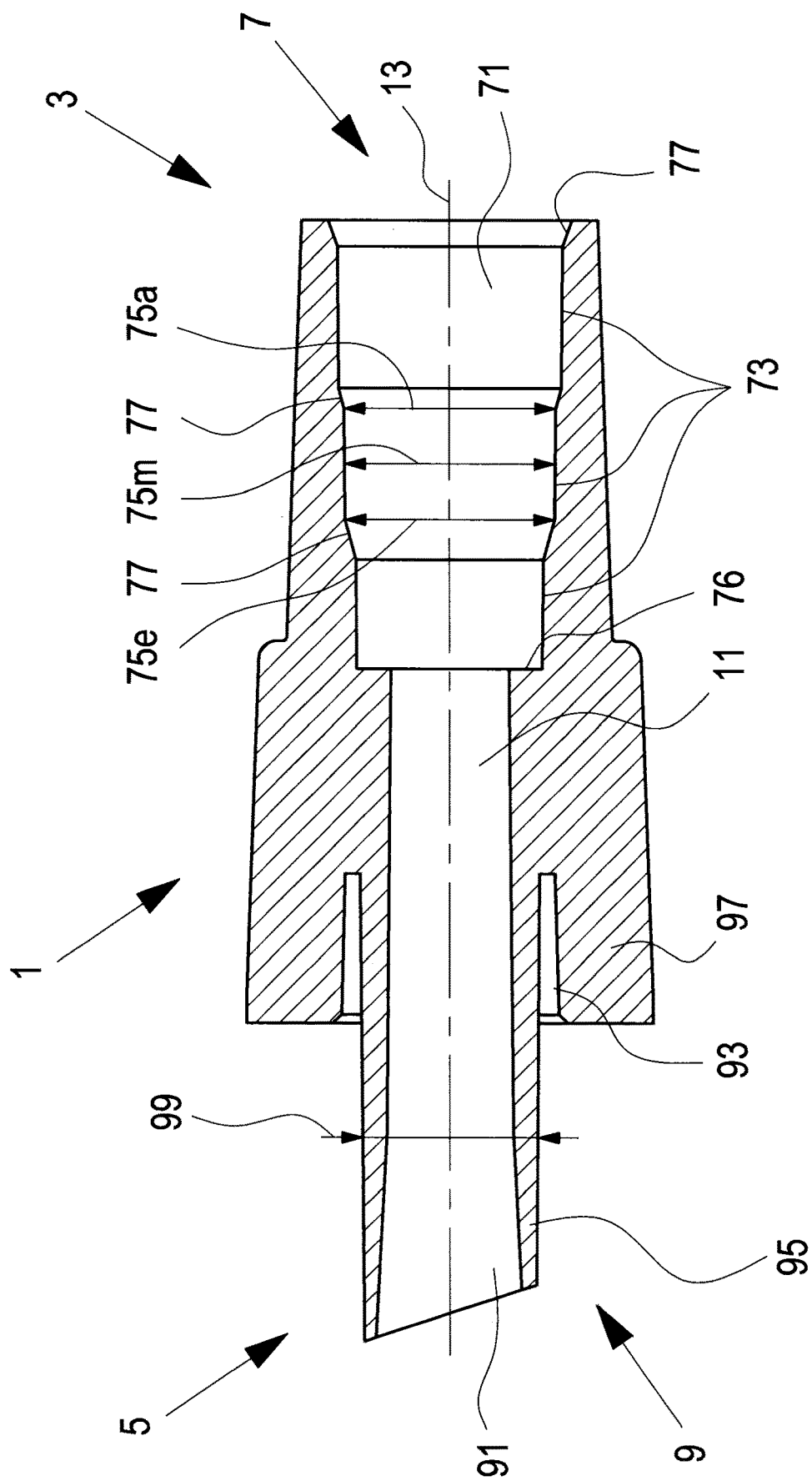
FIG. 1: a sectional view of an embodiment of the connector device for gastric calibration hoses.

The connector device 1 for gastric calibration hoses 2 comprises a first end 3 and an opposite second end 5, wherein a first connector means 7 is formed at the first end 3 and a second connector means 9 is formed at the second end 5. The first and the second connector means 7, 9 are in communication with each other via a fluid channel 11. The first connector means 7 has a first tapering cavity 71 into which gastric calibration hoses 2 may be plugged for fluidic coupling. The embodiment of a connector device 1 illustrated further comprises a second connector means 9 for coupling different medical devices 4 thereto, which has a second tapering cavity 91 and a tapering recess 93 annularly surrounding the second cavity 91. Different medical devices 4 may selectively be inserted, and thus coupled, into the second tapering cavity 91 or, as an alternative, into the tapering recess 93 for fluidic coupling.

In the embodiment illustrated the connector device is designed with a cylindrical or circular cylindrical shape, with a longitudinal axis 13 of the connector device 1.

In the embodiment illustrated the first cavity 71 tapers from the region of the first end 3 towards the second end 5, and the second cavity 91 tapers from the region of the second end 5 towards the first end 3. Further, in the embodiment illustrated, the first tapering cavity 71 and the second tapering cavity 91 are realized such that they respectively form a part of the fluid channel 11. In particular, the second tapering cavity 91 opens directly into the first tapering cavity 71, wherein a step 76 is formed due to the different diameters.

In the embodiment illustrated a delimiting wall 99 and an outer wall 97 surrounding the recess 93 are formed between the second cavity 91 and the recess 93. Here, as shown in the embodiment illustrated, the outer wall 97 may be designed to be recessed towards the first end 3 opposite the delimiting wall 95, such that the delimiting wall 95 forms the second end 5 of the connector device 1.

Further, in the embodiment of the connector device 1 illustrated, it is provided that the outer diameter 99 of the delimiting wall 95 continuously increases from the region of the second end 5 towards the first end 3. Further, the delimiting wall 95 is chamfered in the region of the second end 5 with respect to the longitudinal axis 13. Due to the chamfered design of the delimiting wall 95 an oval opening for the second connector means 9 is formed in the region of the second end 5, such that medical devices 4 to be coupled via the cavity 91 can be inserted more easily into the cavity 91.

The annular recess 93 is designed to be tapering continuously from the region of the second end 5 towards the first end. Form the region of the first end 3 towards the second end 5, the first cavity 71 comprises three contiguous, respectively tapering steps 73 for receiving gastric calibration hoses 2 with different average diameters 75m. The three steps 73 illustrated each have different initial diameters 75a and end diameters 75e. The respective average diameter 75m of the three steps 73 decreases step-wise from the first end 3 towards the second end 5.

The first cavity 7 illustrated has an inclined chamfer 77 in the region of the first end 3, while two inclined chamfers 77 are also formed at the two transitions of the three steps 73.

Figure 2A:
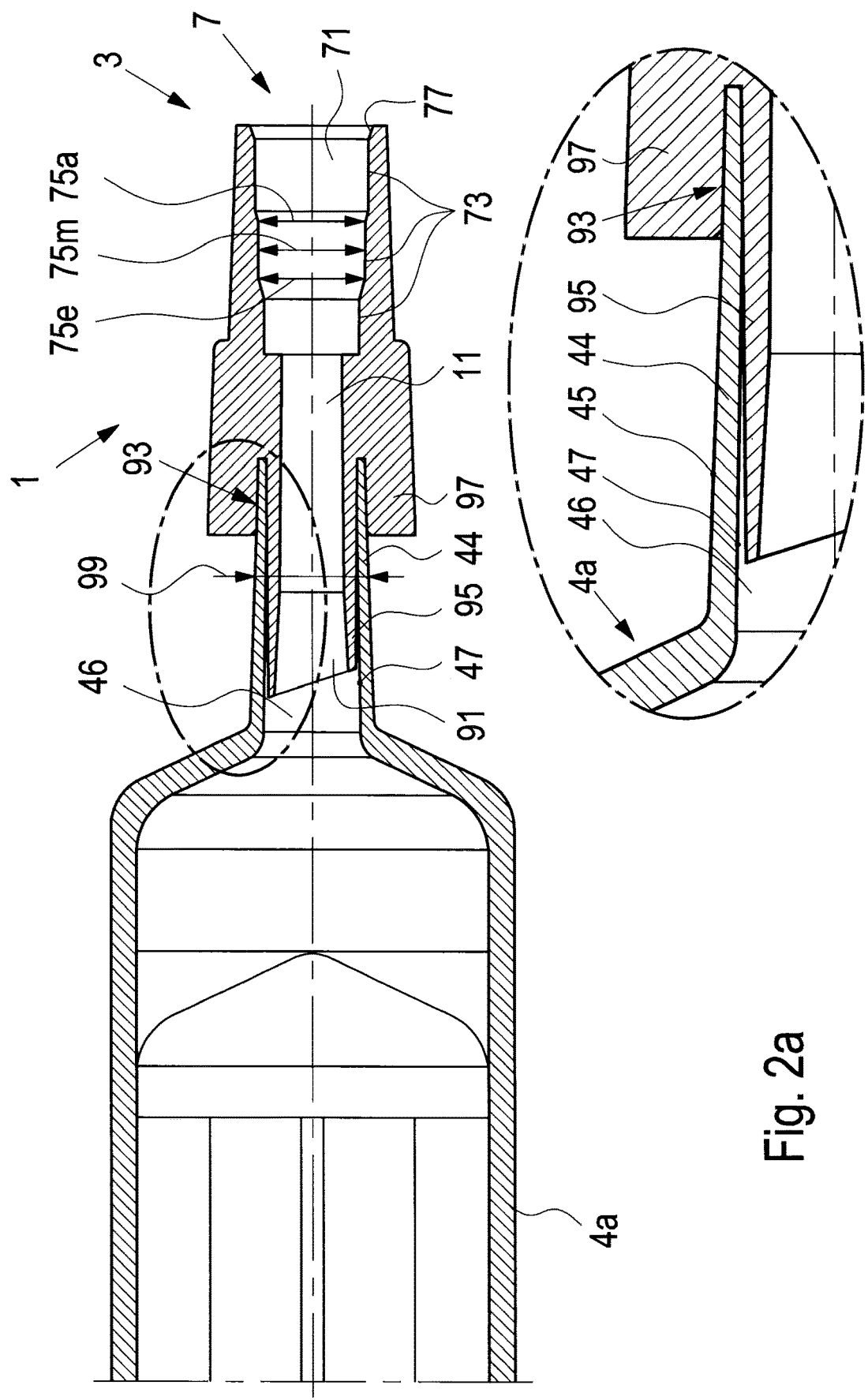
FIG. 2a: a longitudinal section of a connector device with a large syringe coupled thereto.

In FIG. 2a the connector device 1 is illustrated with a syringe device 4a coupled via the tapering recess 93 of the second connector means 8, the syringe device serving as an example for a medical device 4 to be coupled. As can be seen in FIG. 2a, the medical device 4 to be coupled, or in particular the syringe device 5a illustrated, is dimensioned such that the side wall of the connector cone 44 of the syringe device 5a is received in the recess 93 of the connector device 1. For coupling the syringe device 4a to the connector device 1, first, the delimiting wall 95 is inserted into the syringe opening 46. Thereafter, the syringe device 4a and the connector device 1 are moved towards each other substantially along the longitudinal axis 13 such that the outer wall 45 of the connector cone 44 first comes into contact the outer wall 97 surrounding the recess 93. Here, the inner wall 47 of the connector cone 44 of the syringe device 4a and the delimiting wall 95 do not come into contact at the second end 5 of the delimiting wall 95. The outer diameter 99 of the outer wall 95 increases only along the further extension of the outer wall 95 towards the first end 3, such that the inner wall 47 contacts the delimiting wall 95 in the region of the annular recess 93.

The wall of the connector cone 44 of the syringe device 4a may, as illustrated in FIG. 2a, preferably be clamped in the tapering cavity 93 between the delimiting wall 95 and the outer wall 97. Due to the front part of the connector cone 44 being clamped on both sides, the same can be elastically deformed locally, whereby an additional sealing can be obtained between the syringe device 46 and the connector device 1.

Figure 2B:
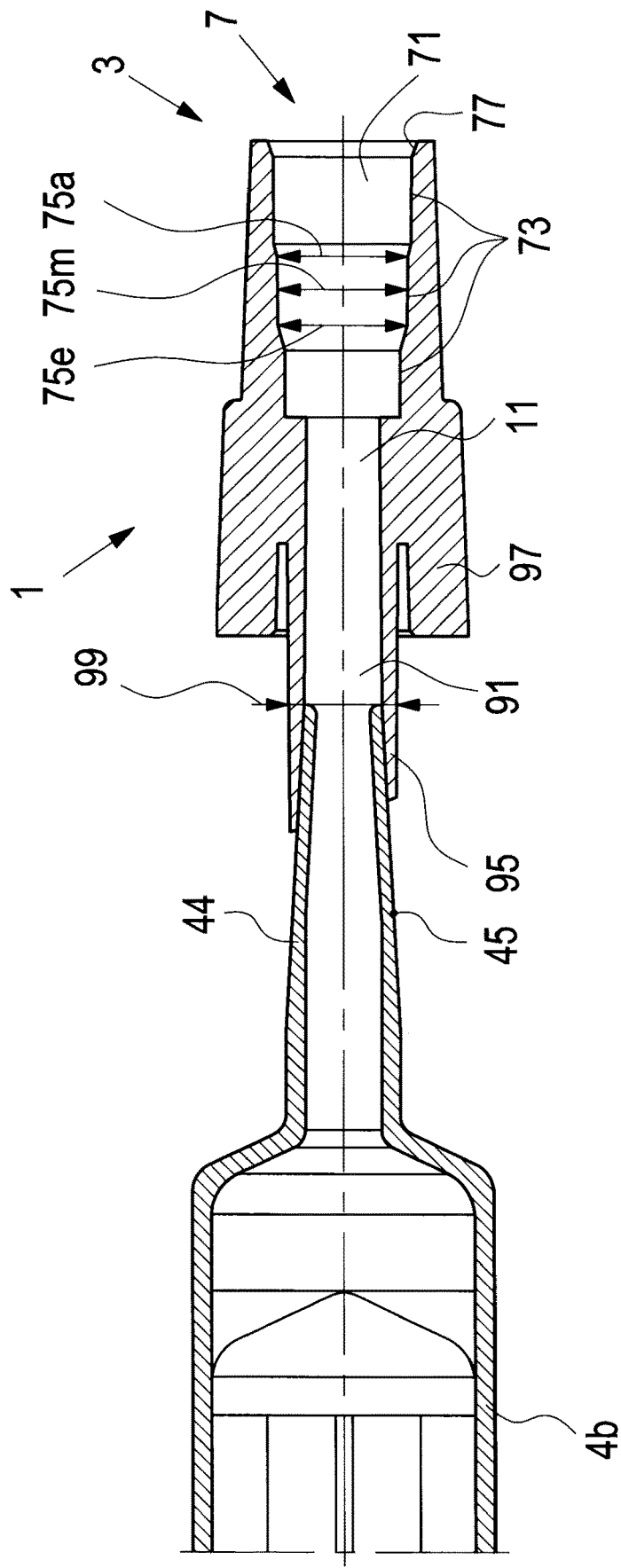
FIG. 2b: a longitudinal section of a connector device with a small syringe coupled thereto.

FIG. 2b illustrates the connector device 1 with a second syringe device 4b coupled thereto via the tapering cavity 91, the syringe being smaller than the one in FIG. 2a. The second syringe device 4b has significantly smaller dimensions compared to the first syringe device 4a, in particular in the region of the connector cone 44. For coupling the syringe device 4b to the connector device 1, the connector cone 44 of the syringe device 4b is inserted into the second tapering cavity 91, where the outer wall 45 finally makes contact with the delimiting wall 95 delimiting the first tapering cavity 71. Due to the above contact of the outer wall 45 with the inner wall surface of the delimiting wall 95, a sealing is ensured between the syringe device 4b and the connector device 1.

Figure 2C:
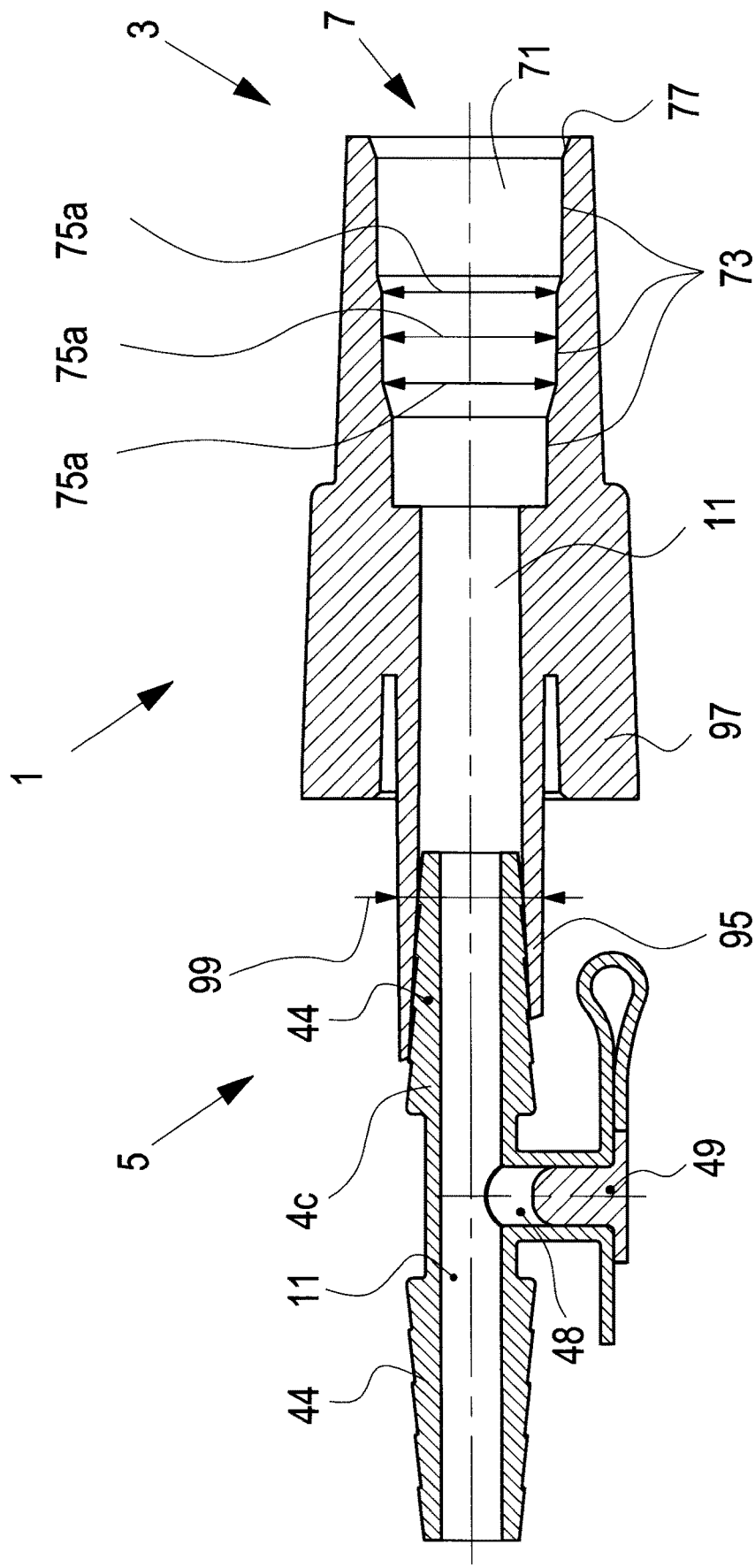
FIG. 2c: a longitudinal section of a connector device with a fingertip coupled thereto.

As can be seen in FIG. 2c, it is also possible, via the first tapering cavity 71, to couple a so-called fingertip 4c to the connector device 1. The fingertip 4c has a fluid channel with two opposite connector cones 44, as well as a lateral opening 48 of the fluid channel 11. In FIG. 2c, the lateral opening 48 is sealed by means of a closure 49. The fingertip 4c is coupled to the connector device 1 via the right connector cone 44 illustrated in FIG. 2c and via the second tapering cavity 91. The coupling is effected analogous to the above specification referring to FIG. 2b.

Figure 3:
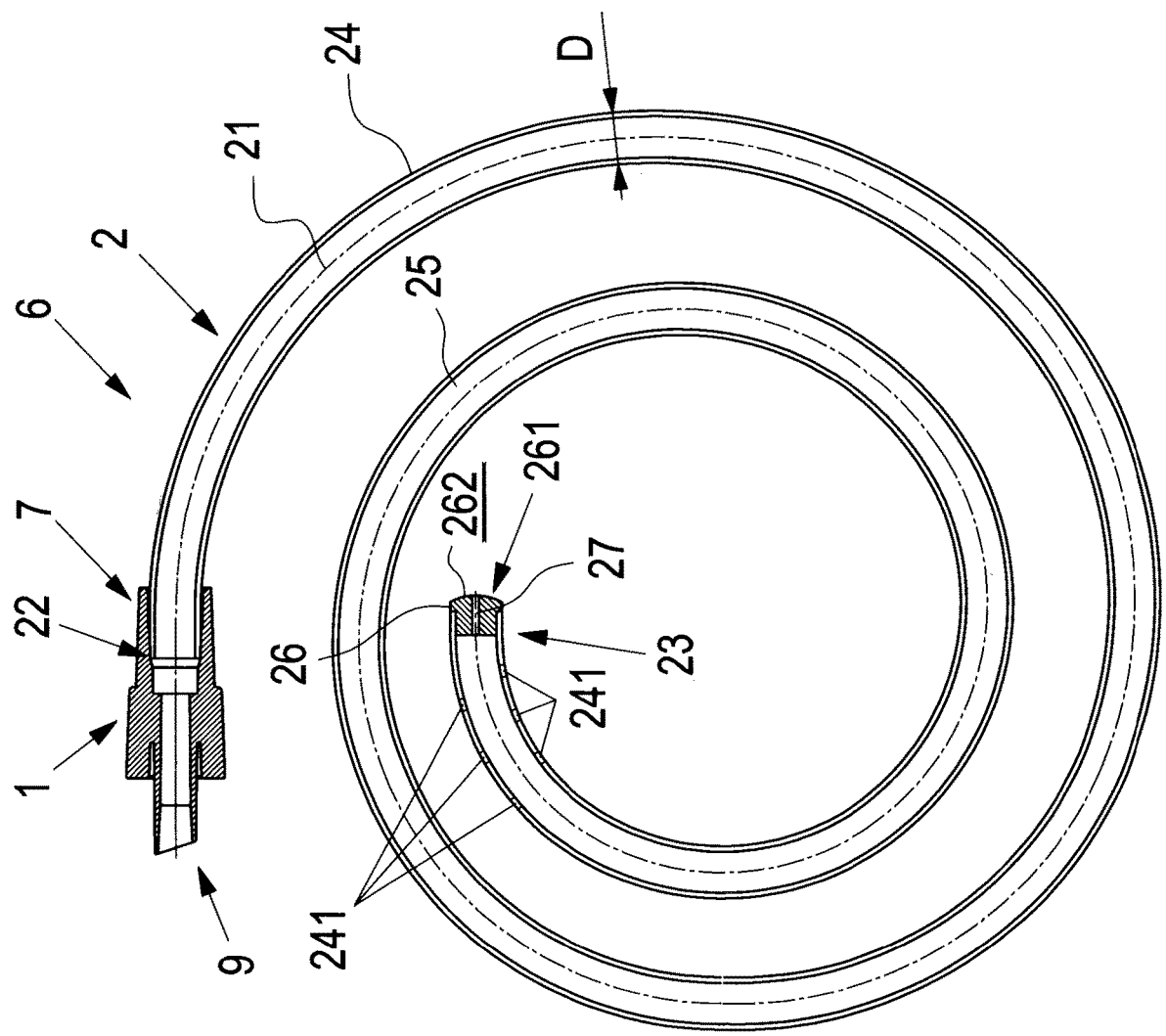
FIG. 3: a sectional view of a medical system comprising a gastric calibration hose coupled to a connector device.

FIG. 3 illustrates a medical system 6 comprising a connector device 1, as well as a gastric calibration hose 2. The gastric calibration hose 2 has a hose longitudinal axis 21, a first and an opposite second hose end 22, 23 and a hose wall 24 enclosing a lumen 25. At the second hose end 23, an end element 26 is arranged which delimits the lumen 25, wherein the end element 26 has a passage 27 substantially parallel to the hose longitudinal axis 21 and extending through the end element 26. The first hose end 22 of the calibration hose 2 is coupled to the connector device 1 via the first connector means 7. In the embodiment illustrated the hose wall 24 of the calibration hose 2 has a plurality of openings 241 in the region of the second hose end 23.

At its end 261 averted from the hose, the end element 26 has a rounded surface 262.

Figure 4:
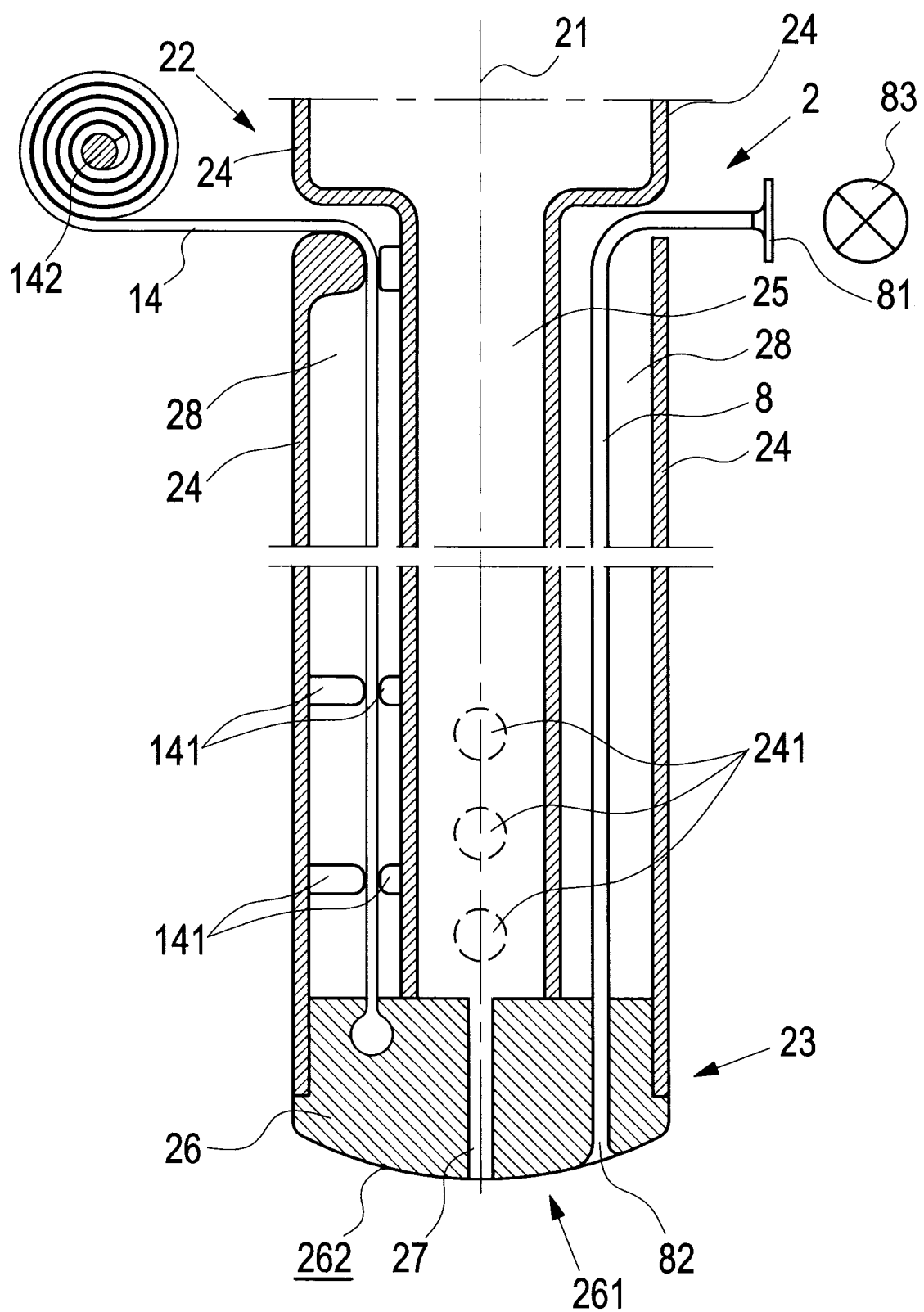
FIG. 4: a sectional view of another embodiment of a gastric calibration hose.

FIG. 4 illustrates a schematic diagram of another embodiment of a gastric calibration hose 2 in sectional view. The gastric calibration hose 2 is basically formed by a hose wall 24 with a first hose end 22 and an opposite second hose end 23 to which a end element 26 is fastened. Together with the end element 26, the hose wall 24 delimits a lumen 25, wherein the lumen 25 is in fluid communication with its environment via the three openings 241 and the passage 27 formed in the end element 26. At the first hose end 22, the hose wall 24 is designed such that a connector device 1 (not illustrated) can be coupled thereto such that the calibration hose 2 can form a medical system 1 together with the connector device 1. In the embodiment illustrated, the hose wall 24 is of a double-walled design except for the region of the first hose end 22, so that two auxiliary channels 28 are formed, wherein, in the region of the second hose end 23, the two auxiliary channels each terminate in the end element 26 and, in the region of the first hose end 22, are guided to the outside through openings via the hose wall 24. Therefore, there is no fluid communication between the auxiliary channels 28 and the lumen 25.

In the auxiliary channel 28 illustrate on the left in FIG. 4, a cable pull means 14 is guided by a plurality of cable pull guides 141 for sliding movement in the longitudinal direction with respect to the hose wall 24, and is connected to the end element 26 in the region of the latter. In the region of the of the first hose end 22, the cable pull means 14 is guided to the outside via an opening in the hose wall 24, where a reeling means 142 is arranged. Using the reeling means 142, it is possible to reel up the cable pull means 14 and to thereby shorten the portion of the cable pull means 14 located inside the auxiliary channel 28. Due to the flexibility of the hose wall 24 the hose 2 bends when the cable pull means 14 is reeled upon the reeling means 142. In the second auxiliary channel 28, a light conductor means 8 is guided, which extends through the end element 28 in the region on the second hose end 23, wherein a light emission means 82 is formed at the end 261 of the end element 26 averted from the hose. The opposite end of the light conductor means 8 is again guided to the outside in the region of the first hose end 22 via the hose wall 24, where a light entrance means 81 is provided at the light conductor means 8. By means of a light source 83 light waves can be coupled into the light conductor means 8 via the light entry means 81 and can be guided to the light emission means 82 along the hose longitudinal axis 21 through the auxiliary channel 28 and the end element 26. The light waves are coupled out at the light emission means 82 and illuminate the region in front of the second hose end 23.

The invention claimed is:

1. A connector device for gastric calibration hoses comprising:
    a first end and a second end opposite the first end;
    a first connector disposed at the first end;
    a second connector disposed at the second end, and connected with the first connector via a fluid channel;
    the first connector comprising a first tapering cavity sized and shaped to receive and couple with a gastric calibration hose;
    the second connector comprising a second tapering cavity and a tapering recess annularly surrounding the second tapering cavity;
    an outer wall surrounding the tapering recess and a delimiting wall;
    wherein the second tapering cavity and the tapering recess are sized and shaped to alternatively couple with different medical devices by receiving therein tubular structures of the different medical devices;
    wherein the tapering recess is elongated, along the entire length of the tapering recess, in a direction from the second end towards the first end;
    wherein the tapering recess tapers continuously along the entire length of the tapering recess;
    wherein the tapering recess includes an inner annular surface extending in the direction from the second end towards the first end, and an outer annular surface extending in the direction from the second end towards the first end;

wherein both the inner annular surface and the outer annular surface extend linearly, in cross-section, in the direction from the second end towards the first end; and wherein the delimiting wall is chamfered in a region of the second end with respect to a longitudinal axis of the connector device, such that an end face of the delimiting wall is angled along an inclined plane at an oblique angle with respect to the longitudinal axis of the connector device, the end face of the delimiting wall defining and annularly surrounding an opening for the second connector in the region of the second end; and wherein the second tapering cavity includes a first tapering section and a second section, the first tapering section extending from the angled end face of the delimiting wall until the second section and the second section extending from the first tapering section until the first tapering cavity, the first tapering section being annularly surrounded by the delimiting wall, an inner diameter of the delimiting wall at the first tapering section decreasing linearly, in cross-section, from the angled end face of the delimiting wall until the second section, an inner diameter of the second section tapering linearly at a smaller angle than the first tapering section.

2. The connector device of claim 1, wherein the first tapering cavity tapers from the first end towards the second end and the second tapering cavity tapers from the second end towards the first end.

3. The connector device of claim 1, wherein the first tapering cavity and/or the second tapering cavity form a part of the fluid channel.

4. The connector device of claim 1, wherein the delimiting wall is disposed between the second tapering cavity and the tapering recess, wherein the outer wall is set back towards the first end with respect to the delimiting wall, such that the delimiting wall forms the second end.

5. The connector device of claim 4, wherein an outer diameter of the delimiting wall increases from the second end towards the first end.

6. The connector device of claim 4, wherein the end face of the delimiting wall defines an oval opening for the second connector in the region of the second end.

7. The connector device of claim 1, wherein a dimension of the first tapering cavity is adapted to an outer diameter of the gastric calibration hose to be coupled thereto, the outer diameter being in a range between approximately 40 to 45 Fr.

8. The connector device of claim 1, wherein from the first end towards the second end, the first tapering cavity comprises at least two contiguous, respectively tapering steps for receiving gastric calibration hoses with different average diameters, wherein the steps have different initial and end diameters, and wherein a respective average diameter of the steps respectively decreases continuously from the first end towards the second end.

9. A medical system comprising a connector device of claim 1, as well as a gastric calibration hose, wherein the gastric calibration hose comprises:
at least a hose longitudinal axis,
a first hose end and a second hose end opposite to the first hose end, and
a hose wall that encloses a lumen,
wherein an end element is arranged at the second hose end, delimiting the lumen, wherein the end element comprises at least one passage extending through the end element in a manner substantially parallel to the hose longitudinal axis,
wherein the first hose end is coupled to the connector device via the first connector.

10. The medical system of claim 9, wherein the hose wall has a plurality of openings in a region of the second hose end.

11. The medical system of claim 9, wherein the gastric calibration hose comprises an auxiliary channel, wherein the auxiliary channel encloses a volume and extends substantially parallel to the hose longitudinal axis, wherein an end of the auxiliary channel opens into the end element.

12. The medical system of claim 11, wherein a light conductor device is provided in the auxiliary channel, wherein a light entry surface is formed at the light conductor device in a region of the first hose end, and wherein, in the second hose end, the light conductor device extends through the end element to an end averted from the hose, where at least one light emission means is arranged.

13. The medical system of claim 11, wherein in the auxiliary channel, a cable pull means is guided for sliding movement in the longitudinal direction with respect to the hose wall, wherein the cable pull means is fastened at the second hose end, and, in a region of the first hose end, is guided out from the hose wall via the auxiliary channel.

14. The medical system of claim 13, wherein in the auxiliary channel guiding the cable pull means, a plurality of cable pull guides are arranged along the hose longitudinal axis, spaced from each other.

15. The medical system of claim 14, wherein the cable pull guides are fastened to the auxiliary channel or are formed integrally with the auxiliary channel.

16. The medical system of claim 13, wherein a means for shortening a part of the cable pull means guided in the auxiliary channel is arranged in the region of the first hose end.

* * * * *